United States Patent [19]

Bollen et al.

[11] Patent Number: 4,828,988

[45] Date of Patent: May 9, 1989

[54] HYBRID POLYPEPTIDES COMPRISING SOMATOCRININE AND ALPHA$_1$-ANTITRYPSIN, METHOD FOR THEIR PRODUCTION FROM BACTERIAL CLONES AND USE THEREOF FOR THE PRODUCTION OF SOMATOCRININE

[75] Inventors: Alex J. Bollen, Itterbeek; Paul Jacobs, Lanquesaint, both of Belgium

[73] Assignee: Smith Kline - RIT, Rixensart, Belgium

[21] Appl. No.: 863,281

[22] Filed: May 15, 1986

[51] Int. Cl.$^4$ .................. C12P 21/00; C12P 21/02; A61K 37/43; C07K 1/00; C12N 15/00
[52] U.S. Cl. .................................. 435/68; 435/69; 435/70; 435/91; 435/172.3; 435/320; 435/252.33; 435/849; 935/47; 935/13; 935/29; 935/60; 935/73; 530/313; 530/324; 530/343; 530/350; 530/380; 530/402; 530/407
[58] Field of Search ............... 435/68, 70, 172.3, 253, 435/69, 320; 935/48, 47, 13, 29, 73, 60; 536/27; 530/313, 324, 343, 350, 380, 402, 407

[56] References Cited

U.S. PATENT DOCUMENTS

| | | | |
|---|---|---|---|
| 4,546,082 | 10/1985 | Kurjan et al. | 435/68 |
| 4,617,149 | 10/1986 | DiMarchi et al. | 435/317.1 |
| 4,689,318 | 8/1987 | Kaiser et al. | 514/12 |

FOREIGN PATENT DOCUMENTS

| | | | |
|---|---|---|---|
| 3707184 | 12/1984 | Australia | 435/68 |
| 901119 | 3/1985 | Belgium | 435/68 |
| 0129073 | 12/1984 | European Pat. Off. | 435/68 |
| 0134085 | 3/1985 | European Pat. Off. | 435/68 |

OTHER PUBLICATIONS

Cravador et al, *Biochimie*, vol. 67 (7-8), pp. 829–834 Jul. 1985, "Total DNA Synthesis and Cloning in *Escherichia coli* of a Gene Coding for the Human Growth Hormone Releasing Factor".

Guillemin et al., *Science*, 218:585 (1982).

*Primary Examiner*—Robin Teskin
*Attorney, Agent, or Firm*—Edward T. Lentz; Janice E. Williams; Alan D. Lourie

[57] ABSTRACT

A fusion between DNA sequences coding for hAT and hGRF via a synthetic adaptor coding for an in vitro cleavable amino acid sequence is used to express hGRF at high levels in *E. coli*.

19 Claims, No Drawings

HYBRID POLYPEPTIDES COMPRISING SOMATOCRININE AND ALPHA$_1$-ANTITRYPSIN, METHOD FOR THEIR PRODUCTION FROM BACTERIAL CLONES AND USE THEREOF FOR THE PRODUCTION OF SOMATOCRININE

FIELD OF THE INVENTION

The present invention relates to hybrid polypeptides comprising somatocrinine and alpha$_1$-antitrypsin, to a method for their production from bacterial clones and to the use thereof for the production of somatocrinine.

More precisely, the method and use of this invention consists of a series of steps comprising linking, in frame, via a synthetic DNA adaptor coding for an in vitro cleavable amino acid sequence, a nucleotide sequence corresponding to somatocrinine, i.e. mature human growth hormone releasing factor or an active fragment or derivative thereof and at least a fragment of the sequence coding for human alpha$_1$-antitrypsin which expresses itself in an optimal manner in E. coli; introducing the linked sequences into a strong bacterial expression vector; producing therein the hybrid polypeptide and cleaving in vitro said hybrid polypeptide to yield somatocrinine.

BACKGROUND OF THE INVENTION

The factor for release of the human growth hormone, also called somatocrinine (hereinafter designated by the abbreviation "hGRF") is a positive regulator for the secretion of growth hormone (hereinafter designated by the abbreviation "GH") by the adenohypophysis. hGRF has been isolated from a human pancreatic tumor causing acromegaly; it is a polypeptide of 44 amino acids which has been sequenced (Guillemin et al., Science 218, 585–587, 1982). Antibodies against this peptide have enabled identification of an immunoreactive material in the hypothalamus of various primates and an apparently identical polypeptide has also been isolated from the human hypothalamus. Finally, experiments of the "southern blot" type indicate that there is only a single gene coding for hGRF. This, therefore, suggests that the tumoral pancreatic factor is coded by the same mRNA as the physiological hypothalamic factor. The usefulness of being able to produce substantial amounts of human GRF is due in particular to the fact that its genetic or physiological deficiency is a cause of dwarfism; that its stimulating effect on the synthesis of growth hormone (GH) should lead to its usefulness in diagnosis of deficiencies or disorders of GH metabolism; that its administration could provide an acceleration in regeneration of tissue, for example, in the treatment of severe burn victims and that it has been shown that the administration of human GRF to animals stimulates their growth.

A form of hGRF having only 40 amino acids residues has also been reported and fragments of GRF having as few as about 27 amino acid residues have been found to be biologically active. The full 44 amino acid residue pancreatic hGRF peptide has been synthesized chemically, and synthetic hGRF, synthetic hGRF fragments, and synthetic analogs thereof represent a potential source of highly potent regulatory substances; however, chemical synthesis of such long peptide chains is quite expensive.

Recombinant DNA techniques by which hGRF DNA is introduced into a cell to express hGRF have also been developed.

However these techniques yield only rather limited amounts of hGRF.

Belgian Pat. No. 898.666 describes such a technique wherein chemically synthesized DNA fragments are combined to DNA fragments isolated from natural source.

The process of the present invention is inspired from the method consisting in producing fused or hybrid proteins from which the desired protein itself is then eventually recovered.

Examples of such methods are the European Patent Application Publication No. 0 020 290 and the German Patent application No. 2922496 which describe the preparation of a protein by selective enzymatic cleavage of the C-terminal from a fusion protein with the N-terminal of a particular tetrapeptide sequence;

the European Patent Application Publication No. 0 133 282 which describes the preparation of a polypeptide amide such as growth hormone releasing factor by producing a glycine peptide by genetic technology and enzymatically removing the C-terminal glycine;

the Australian Patent Application No. 85/37071 which describes the preparation of a fibrinolytically active hybrid protein by different methods among which the method comprising taking the genetic information of each protein, cutting and ligating this to construct a DNA sequence coding for the hybrid protein and expressing this DNA in prokaryote or eukaryote hosts, the separate chains being eventually prepared thereafter by mild reduction to break interchain disulfide bridges followed by affinity chromatography;

the European Patent Application Publication No. 0 134 085 which describes the production of preprohuman pancreatic growth hormone releasing factor (hpGRF) by recombinant DNA technique, using a nucleotide sequence encoding the entire hpGRF peptide sequence, a peptide segment linked to the amino terminal of the hpGRF peptide and a peptide segment linked to the carboxy terminal of the hpGRF peptide, said precursor being converted to GRF when appropriate processing enzymes are present in the transformed cells;

the European Patent Application Publication No. 0 129 073 which describes a process wherein a peptide with growth hormone releasing factor activity is prepared by cultivation of yeast transformed with DNA construct comprising a coding sequence encoding for growth hormone releasing factor and expressing a fused protein.

SUMMARY OF THE INVENTION

According to the present invention, hGRF is prepared by a bacterial clone transformed with a recombinant plasmid vector comprising a DNA sequence coding for hGRF and a DNA sequence coding for human alpha$_1$-antitrypsin (hAT) or at least a fragment thereof encompassing the codons from about amino acid 2 or about amino acid 15 to about amino acid 363, both sequences being fused in frame via a synthetic DNA adaptor carrying the information corresponding to the amino acid sequence (Asp)$_4$Lys.

The process of the present invention can be schematized by the following series of steps:

(1) preparation of a DNA sequence coding for hGRF or for an active fragment or derivative thereof prepared by full chemical synthesis or by reverse transcription or by a combination thereof, preferably by full chemical synthesis, preferably starting at the codon for amino acid 1 of the polypeptide.

(2) isolation of a DNA fragment coding for human alpha$_1$-antitrypsin prepared by full chemical synthesis or by reverse transcription or by a combination thereof, preferably by reverse transcription and encompassing the codon from about amino acid 2 or about amino acid 15 to about amino acid 363.

(3) preparation of a synthetic DNA adaptor carrying the information corresponding to the amino acid sequence (Asp)$_4$Lys which is cleavable in vitro by the enzyme enterokinase and appropriate restriction sites for the fusion in frame of hAT and hRGF sequences.

(4) fusion, in frame, and read from the 5' to the 3' end, of a hAT coding sequence, a synthetic DNA adaptor coding for an amino acid sequence cleavable in vitro and the hGRF gene, i.e. in the order hAT-cleavable sequence-hGRF.

(5) insertion of the fused sequence into a strong bacterial expression vector.

(6) transformation of a host E. coli bacterium with the recombinant plasmid vector.

(7) selection of the transformed bacteria which carry the recombinant plasmid.

(8) production of the corresponding hybrid polypeptide in a transformed E. coli bacterium.

(9) cleavage in vitro of the hybrid polypeptide produced in E. coli cells by the enzyme enterokinase.

(10) obtention of mature hGRF and its characterization by immunological methods.

More particularly and for instance, this series of steps comprises :

(1) obtaining a 135 bp DNA fragment coding for hGRF by digesting the DNA of an appropriate plasmid (e.g. pULB1113 described in Belgian Pat. No. 898.666) with the enzymes RsaI and SalI.

(2) obtaining a 1081 or a 1044 bp DNA fragment coding for all or part of hAT, i.e. from amino acid 2 or 15 to 363, by digesting the DNA of an appropriate plasmid (e.g. pULB1523 described in Belgian Pat. No. 895.961) with the enzymes BamH1 or BclI and AvaI.

(3) synthesizing a 27 base long oligomer and a 23 complementary counterpart which by annealing constitute the synthetic DNA adaptor coding for the (Asp)$_4$Lys amino acid sequence cleavable in vitro by the enzyme enterokinase and carrying appropriate restriction sites.

(4) ligating with T4 DNA ligase to the synthetic adaptor the DNA fragments corresponding to hGRF and hAT in order to obtain a fusion in frame.

(5) inserting the ligated DNA sequences into the DNA of strong bacterial expression vector carrying a thermoinducible promotor (e.g. the DNA of plasmid pAS1.

(6) transforming a lysogenic bacterium (more particularly a lysogenic E. coli strain e.g. the AR58 strain) with the plasmid of step 5.

(7) on basis of antibiotic resistance, selecting bacterial clones which carry said plasmid.

(8) producing the hybrid polypeptide in a transformed bacterium by inducing the promotor carried by the rcombinant plasmid.

(9) cleaving the hybrid polypeptide with enterokinase.

(10) characterizing by reaction with antibodies against hGRF the mature hGRF resulting from the cleavage of the hybrid polypeptide.

DETAILED DESCRIPTION OF THE INVENTION

It has now been found that expression of hGRF in bacteria can be significantly and unexpectedly improved by fusing the coding sequence for hGRF to a coding sequence corresponding to hAT or a fragment thereof which expresses itself in an optimal manner in bacteria, such that the direction at transcription is hAT to hGRF. Using the recombinant DNA molecule of the invention, hGRF is then produced in bacteria in large amount whereas no hGRF is detected when its corresponding DNA sequence is cloned as such in a bacterial expression vector (CRAVADOR et al., Biochimie 67, 829, 1985).

More particularly, the coding sequence within the recombinant molecule of this invention comprises (1) the fragment of the sequence coding for hAT extending from the codon for about amino acid 2 or about amino acid 15 to about amino acid 363. (2) a synthetic nucleotide coding for the (Asp)$_4$Lys peptide which is cleavable in vitro by enterokinase using standard enzymological techniques and (3) a DNA sequence for hGRF starting at the codon specifying the amino acid 1 of the mature molecule. This sequence has been obtained by standard chemical synthesis as described by CRAVADOR et al. (loc. cit.) and in Belgian Pat. No. 898.666. The plasmid expression vector used in this invention employs the leftward promotor (P$_L$) of lambda and the cII ribosome binding site. The construction of the recombinant plasmid is described in the following example below wherein the expression data were obtained by heat induction (Meth. Enzym. 101, 123, 1983). The resulting hybrid polypeptide thus comprises N-hAT-enzyme cleavage site-hGRF-C.

It is obvious that the recombinant DNA molecules described in this specification are purely illustrative and not limitative of the invention. Alternative constructions can be made by techniques well known in the field of molecular genetics. The effects of these alternative constructions on expression levels in bacteria can be readily determined by well known techniques such as ELISA as disclosed, for example, by BOLLEN et al. (DNA 2, 255, 1983). Other illustrative DNA molecules of the invention are those wherein the size of the hAT coding sequence fused to the hGRF is shorter than the one described in the example below or where the hGRF nucleotide sequence is modified without changing the amino acid sequence.

The expression vector into which the fused DNA sequence coding for hAT and hGRF is inserted to prepare the vector of the invention can be any of the numerous bacterial expression vectors known and available in the field. Regulatable expression vectors are preferred. In this specification, the term "regulatable" means that transcription of the inserted coding sequence is not constitutive, but can be induced, such as by addition of an inducing agent to the culture medium or by heat. Exemplary E. coli expression vectors include, among others, pCQV2, described by QUEEN, C (J. Mol. Appl. Genet. 2, 1-10, 1983), and pAS1 described by M. ROSENBERG et al. (Meth. Enzym. 101, 123-138,1983). pAS1 carries the pBR322 origin of replication, an ampicillin resistance marker and a series of fragments from lambda which comprise the regulatory region, namely, the leftward promoter of lambda (P$_L$), N anti-termination function recognition sites (NutL and NutR), the rho-dependent transcription termination signal (tR1) and the cII ribosome binding site, including the cII translation initiation site, the G residue of which is followed immediately by a BamHI cleavage site as follows:

5'... CATATG*GATC...3' wherein the symbol, *, represents the cleavage site for BamHI.

pAS1 can be derived from pKC30cII by deleting nucleotides from the BamHI site at the cII-pBR322 junction of pKC30cII to the cII ATG and religating the molecule to regenerate the BamHI site immediatey downstream of the ATG. pKC30cII is constructed by inserting a 1.3 kb HaeIII fragment from lambda which carries the cII gene into the HpaI site of pKC30 (SHATZMAN et al., Experimental Manipulation of Gene Expression, Edit. by M. Inouye, Academic Press, New York, 1983 and M. ROSENBERG et al., loc. cit.). pKC30 is described by SHIMITAKE et al. (Nature 292, 128, 1981). It is a pBR322 derivative having a 2.4 kb HindIII-BamHI fragment of lambda inserted between the HindIII and BamHI sites in the tetR gene of pBR322. Constructions similar to pAS1 are described by COURTNEY et al. (Nature 313, 149, 1985) and KOTEWICZ et al. (Gene 35, 249, 1985). The coding sequence is operatively inserted therein, that is, in correct orientation and in proper reading frame to the regulatory element, by standard techniques.

Other cloning and expression systems are known and available for expressing the coding sequence of the invention in other bacteria, e.g. Bacillus, Streptomyces, Corynebacterium and others.

A coding sequence for mature hAT, from which the DNA fragments used in the invention are derived, can be obtained by standard techniques by reverse transcription of selected messenger RNA populations from liver cells such as disclosed, for example, by BOLLEN et al. (Belgian Pat. No. 895.961); BOLLEN et al. (DNA 2, 255, 1983); COURTNEY et al. (European Patent Application Publication No. 0 114 777); KAWASAKI et al. (The Molecular Biology of Yeast, Cold spring Harbour Laboratory, Aug. 16–21, 1983); LONG et al. (Structure and Organization of Genes I, Cold Spring Harbour Laboratory, Abstract No. 25, 1983); WOO et al. (From Gene to Protein: Translation into Biotechnology, edit. by Ahmed et al., Academic Press, New York, 1982); KURACHI et al. (Proc. Natl. Acad. Sci. USA 78, 6826, 1981); PARKER et al. (Australian Patent Application No. 31801/84) and COSTANZO et al. (EMBO J. 2, 57, 1983), all of which are incorporated herein by reference as though fully set forth.

A fully synthetic DNA coding for hGRF can be obtained by standard procedure well known in the field such as disclosed, for example, by CRAVADOR et al. (Belgian Pat. No. 898.666) and by CRAVADOR et al. (Biochimie 67, 829, 1985) or by BARR et al (European Patent Application Publication No. 0 129 073). The hybrid polypeptides of the invention are bridged hAT/hGRF polypeptides; they are produced by culturing microorganisms or cells which have been transformed with the expression vector of the invention under permissive conditions. By "permissive conditions" is meant culture conditions, e.g. analytes, metabolites, other medium ingredients and temperature, under which expression of said hybrid protein is induced. Typically, transformed E. coli are cultured in a nutrient broth containing assimilable sources of carbon and nitrogen, with aeration and under selection pressure, until log phase growth ($A_{650}$ about 0.4–0.6) prior to induction and then for an additional 1-½ to 5 hours following induction until a recoverable quantity of the polypeptide is expressed.

The hybrid polypeptides of the invention expressed in E. coli or other organisms are isolated from the producing culture by standard protein isolation techniques.

Typically, the purification scheme comprises (1) disruption of cells, (2) clarification of the cellular extract, (3) separation of the hybrid hAT/hGRF polypeptide and (4) final purification to remove contaminants. The first step can be accomplished for instance by addition of lysozyme or other lysing or permeabilizing agent or by mechanical or ultrasonic disruption. Other means for externalizing the polypeptide include use of temperature-sensitive lytic bacteria such as described by AUERBACH and ROSENBERG (European Patent Application Publication No. 0 140 864). When the hybrid polypeptide is precipitated within the cell extract, it can be resolubilized by addition of a denaturant. Such techniques are well known in the art. Several of these are reviewed by BUILDER et al. (European Patent Application Publication No. 0 114 506). The hybrid hAT/hGRF molecules specifically examplified herein are soluble in standard E. coli extracts.

The soluble bridged hAT/hGRF molecules of the invention can be separated by standard techniques.

Cleavage of the bridged hAT/hGRF molecules of the invention can be achieved by enzymatic digestion with the enzyme enterokinase under standard conditions such as those described by MAROUX et al. (J. Biochemistry 246, 5031, 1971). Mature hGRF resulting from the cleavage can then be separated by standard chromatography methods such as those involving molecular sieves. A preferred purification process comprises an affinity chromatography employing supported hGRF polyclonal or monoclonal antibody which separates the cleaves hGRF from the hAT molecules.

The so-obtained polypeptides or the nontoxic salts thereof, combined with a pharmaceutically or veterinarily acceptable carrier to form a pharmaceutical composition, may be adminstered to humans and animals either intravenously, subcutaneously, intramuscularly, percutaneously, e.g. intranasally or even orally, as well known in the art. The administration may be employed to stimulate the release of GH (Growth Hormone) where the host being treated requires such therapeutic treatment. The required dosage will vary with the particular condition being treated, with the severity of the condition and with the duration of desired treatment.

Such peptides are often administered in the form of nontoxic salts, such as acid addition salts or metal complexes, e.g. with zinc, iron or the like (which are considered as salts for purposes of this application). Illustrative of such acid addition salts are hydrochloride, hydrobromide, sulfate, phosphate, maleate, acetate, citrate, benzoate, succinate, malate, ascorbate, tartrate and the like. If the active ingredient is to be orally administered in tablet form, the tablet may contain a binder, such as tragacanth, corn starch or gelatin, a disintegrating agent, such as alginic acid, and a lubricant, such as magnesium stearate. If administration in liquid form is desired, sweetening and/or flavoring may be used, and intraveous administration in isotonic saline, phosphate buffer solutions or the like may be effected.

The peptides should be administered to humans under the guidance of a physician, and pharmaceutical compositions will usually contain the peptide in conjunction with a conventional, solid or liquid, pharmaceutically acceptable carrier. Usually, the parenteral dosage will be from about 0.01 to about 1 microgram of the peptide per kilogram of the body weight of the host.

In the following example which—as indicated above—is illustrative and not limitative of the invention, all restriction endonucleases are obtained from commercial sources and are used substantially in accordance with the vendor's instructions.

EXAMPLE

Step 1

The human hAT gene is isolated from the cDNA clone pULB1523 (described in Belgian Pat. No. No. 895.961). The gene is obtained on a PstI fragment encompassing the entire cDNA clone. The fragment is digested with the restriction endonucleases BamH1 and AvaI; it carries the coding sequence for amino acids 2 to 363 of hAT.

Step 2

The fully synthetic human hGRF is isolated from the clone pULB1113 (described in Belgian Pat. No. 898.666) by digestion with the restriction enzymes RsaI and SalI. The DNA fragment obtained codes for the mature hGRF starting at amino acid 1.

Step 3

The synthetic DNA adaptor, is obtained by the technique described by CRAVADOR et al. (Biochimie 67, 829, 1985). The two single stranded fragments, 27 bp and 23 bp respectively, when annealed as described by CRAVADOR et al. (loc. cit.), generate a double stranded DNA fragment carrying a 5' AvaI cohesive end and a 3' ScaI cohesive end. Those cohesive ends are suitable for the fusion in frame of the BamH1-AvaI hAT fragment to the RsaI-SalI hGRF fragment. In addition, the synthetic adaptor codes for the $(Asp)_4Lys$ amino acid sequence which is cleavable in vitro by the enzyme enterokinase as shown by MAROUX et al. (loc. cit.).

Step 4

The DNA from a plasmid expression vector (e.g. pAS1 described in ROSENBERG et al., Methods in Enzymology 101, 123-138, 1983) is cleaved with the enzymes BamHI and SalI. The large fragment resulting from the digestion is retained, it carries the strong $P_L$(lambda) promoter and an ATG initiation codon.

DNA fragments from steps 1 to 4 are assembled by ligation using standard procedures (MANIATIS et al., Molecular cloning: a laboratory manual, Cold Spring Harbour Laboratory, New York, 1982). The resulting construct (pULB1323) is an expression vector containing the hAT gene fragment fused in frame via a synthetic adaptor to the hGRF gene. The recombinant plasmid pULB1323 carries the fused sequences coding for hAT, the synthetic adaptor and hGRF.

A lysogenic strain of E. coli (e.g. strain AR58 described in MOTT et al. (Proc. Natl. Acad. Sci. USA 82, 88, 92, 1985) is transformed with pULB1323 using standard procedures (MANIATIS et al, loc. cit.) and transformants are grown to log phase prior to heat induction (M. ROSENBERG et al., Meth. Enzymol. 101, 123, 1983).

After the induction period, cells are collected by centrifugation and lysed by addition of a lysozyme solution (1 g cells/10 ml solution) 50 mM Tris pH 8; 0,1 mM sodium ethylenediaminetetraacetate (EDTA); 0.1 mM dithiothreitol (DTT); 0.1% Triton X100; 25% sucrose and 0.5 mg/ml of lysozyme. The suspension is then seperated by average-speed centrifugation (20.000 g) for 20 minutes.

Samples of the hybrid hAT/hGRF polypeptide have been analyzed on dodecyl sulfate polyacrylamide gels (LAEMLY, Nature, 227, 680, 1970) and identified by Western blotting and immunodetection (BOLLEN et al., DNA 2, 255, 1983).

The hybrid polypeptide hAT/hGRF coded for by pULB1323 can be detected with antibodies raised either against hAT or against hGRF and this is in sharp contrast with experiments aimed at the expression of mature hGRF such in E. coli where no detection levels can be observed (CRAVADOR), loc. cit.). Furthermore, the hybrid polypeptide has the expected molecular weight for a fusion between hAT ($aa_2$ to $aa_{363}$), the amino acid sequence recognized by enterokinase and mature hGRF. Appropriate controls have been used in the experiment such as uninduced pULB1323 samples, recombinant hAT (induced): idem, uninduced: pAS1 negative control standard hGRF and molecular weight standard.

Samples of the hybrid hAT/hGRF polypeptide have been digested in vitro with enterokinase in order to cleave the hAT/hGRF fusion and release the mature hGRF. The assay consists of an ELISA; it shows that hGRF is released from the hybrid polypeptide which has been bound through its hAT moiety to microwell plates coated with anti hAT antibodies. The assay also shows that bound hAT is not released from the coated microwells during the procedure.

If desired, the cleaved mature hGRF can then be further purified by affinity chromatography in conditions well known in the art or other protein isolation techniques.

We claim:

1. A DNA molecule comprising a fusion in frame and read from the 5' to the 3' end, comprising a DNA sequence which codes for hAT or a DNA sequence which codes for a fragment of hAT which comprises hAT activity, a DNA adaptor sequence which codes for a cleavable amino acid sequence, and a DNA sequence which codes for hGRF or a fragment or derivative of hGRF which fragment or derivative comprises hGRF activity.

2. The DNA molecule of claim 1 wherein the hAT coding sequence is a fragment of the sequence coding for hAT extending from the codon from about amino acid 2 or about amino acid 15 to about amino acid 363.

3. The DNA molecule of claim 1 wherein the adaptor codes for the $(Asp)_4Lys$ amino acid sequence.

4. A bacterial expression vector which comprises the DNA molecule of claims 1; 2 or 3 operably linked to a suitable bacterial regulatory region.

5. The vector of claim 4 which is an E. coli ecpression vector.

6. The vector of claim 6 wherein the expression vector comprises the regulatory region of pAS1.

7. A hybrid polypeptide comprising; hAT or a fragment of hAT which comprises hAT activity, and hGRF or a fragment or derivative of hGRF which fragment or derivative comprises hGRF activity, wherein the hAT or hAT fragment and the hGRF or hGRF fragment or hGRF derivative are covalently bound via an intervening (Asp)$_4$Lys enterokinase cleavage site.

8. The hybrid polypeptide of claim 7 wherein the hAT fragment is the fragment of hAT extending from about amino acid 2 or about amino acid 15 to about amino acid 363.

9. The hybrid polypeptide of claim 7 wherein the hAT fragment is the fragment of hAT extending from amino acid 2 or 15 to amino acid 363.

10. A bacterium transformed with the vector of claim 4.

11. An *E. coli* transformed with the vector of claim 5.

12. An *E. coli* transformed with the vector of claim 6.

13. A method for producing a hybrid polypeptide comprising either hAT or a fragment of hAT which fragment which comprises hAT activity, and hGRF or a fragment or derivative of hGRF which fragment or derivative comprises hGRF activity, which hAT or hAT fragment and hGRF or hGRF fragment or hGRF derivative are bridged by a cleavable amino acid sequence, which method comprises;

(1) transforming a bacterium with a bacterial expression vector which vector comprises operably linked to a suitable bacterial regulatory region a DNA fusion comprising in frame and read from the 5′ to 3′ end, a DNA sequence which codes for hAT or a fragment of hAT which fragment comprises hAT activity, a DNA adaptor sequence which codes for a cleavable amino acid sequence, and a DNA sequence which codes for hGRF, or a fragment or derivative of hGRF which fragment or derivative comprises hGRF activity, (2) culturing the transformed bacterium under conditions permissive for expression of the hybrid polypeptide, and (3) recovering the hybrid polypeptide from the culture medium.

14. The method of claim 13 wherein the transformed bacterium is an *E. coli* and the expression vector is an *E. coli* expression vector.

15. The method of claim 13 wherein the DNA adaptor sequence codes for the (Asp)$_4$Lys enterokinase cleavage site.

16. The method of claim 15 wherein the transformed bacterium is an *E. coli* and the expression vector is an *E. coli* expression vector.

17. The method of claim 13 wherein the hGRF coding DNA sequence codes for the entire hGRF polypeptide.

18. The method of claim 17 wherein the transformed bacterium is an *E. coli* and the bacterial expression vector is an *E. coli* expression vector.

19. A method for producing hGRF or a fragment or derivative of hGRF which fragment or derivative comprises hGRF activity which method comprises;

(1) cleaving the hybrid polypeptide of claims 7, 9 or 10 with enterokinase, and (2) recovering the hGRF or fragment or derivative thereof from the cleavage composition.

* * * * *